United States Patent [19]

Glenn

[11] Patent Number: 5,503,332
[45] Date of Patent: Apr. 2, 1996

[54] SCENT PACKET AND METHOD OF MAKING SCENT PACKET

[76] Inventor: Susa Glenn, P.O. Box 854, Fredericksburg, Tex. 78624

[21] Appl. No.: 56,962

[22] Filed: May 3, 1993

[51] Int. Cl.⁶ .............................. A61L 9/12; B65D 77/04
[52] U.S. Cl. ................... 239/56; 239/34; 428/905
[58] Field of Search ................ 239/34, 53–58, 239/60, 6; 428/905, 34.2, 34.3, 35.2; 206/205

[56] References Cited

U.S. PATENT DOCUMENTS

| | | | |
|---|---|---|---|
| 2,757,957 | 8/1956 | Samann | 239/58 |
| 3,578,545 | 5/1971 | Carson et al. | 428/905 |
| 4,145,001 | 3/1979 | Weyenberg et al. | 239/56 |

FOREIGN PATENT DOCUMENTS 0200580  9/1991  Japan ........................ 239/58

*Primary Examiner*—Karen B. Merritt

[57] ABSTRACT

The invention is of a product and a method for its manufacture, which product is for delivering a desirable scent, such as provided by potpourri products, over a longer period of time than currently available scent delivering products. Applicant's "envelope sachet" includes a wick sheet on which perfume oil is applied, a strip or band of plastic film which is wrapped about the wick sheet, a plastic bag or pouch in which the wick sheet/film strip combination is placed, and an outer paper envelope which is the only outwardly visible aspect of the product when in use. Applicant's envelope sachet produces scent over a substantially longer period of time that conventional sachet and potpourri products using substantially equal portions of perfume oil.

9 Claims, 2 Drawing Sheets

SCENT PACKET AND METHOD OF MAKING SCENT PACKET

BACKGROUND OF THE INVENTION

1. Field of the Invention

Applicant's invention relates to products intended to provide desirable fragrances for home and personal use, as well as methods for effectively manufacturing such products.

2. Background Information

Products for emitting desirable fragrances, particularly for use in home environments, represents a hundreds of millions of dollars per year market in the United States alone. This does not take into account the perfume and cologne markets which are distinct from the product categories to which Applicant's invention relates.

It is common knowledge in the retail industry that the popularity of products such as potpourri, essential oils, sachets, scented candles, and similar scented items (herein collectively referred as "scented gift items") has markedly increased in recent years. As compared with other scented products for which a scent is merely incidental to the product's intended purpose and primary consumer appeal (scented toilet paper, soaps, furniture polishes, for example), scented gift items are purchased primarily for the scent which they provide.

Without question, a foul smelling potpourri will be a commercial failure, no matter what decorative trim or trappings are added. Conversely, scented gift items which provide a particularly attractive scent will likely succeed in the marketplace, particularly if they do so for a prolonged period of time.

It is this last characteristics—scent longevity (time over which the sachet emits a substantially unvarying scent potency)—to which Applicant's invention relates and which has represented a serious short-coming for most scented gift items thus far offered to the public. Anyone having used most of the presently available scented gift items knows that, when used in their intended environments, scent is substantially exhausted in a matter of a two or three weeks (at most).

In recognition of this problem, potpourri companies often sell "refresher oils" to add to existing potpourri products to rejuvenate their scents. Refresher oils are not, however, suitable for use in many environments, such as those in which sachets are used (one would not, for example, want to expose fine clothing and other items close to which sachets are often used to oily substances of any kind). Persons who have used sachets until now simply have to replace them frequently in order to continually enjoy their effects.

Applicants invention addresses these short-comings of presently available sachets.

SUMMARY OF THE INVENTION

It is an object of the present invention to provide a novel sachet product the scent longevity of which is substantially longer than comparable existing products.

It is another object of the present invention to provide a novel sachet product the scent longevity of which is substantially longer than comparable existing products, but the scent intensity of which is substantially constant over the sachet product's useful life.

It is another object of the present invention to provide a novel sachet product the scent longevity of which is substantially longer than comparable existing products, but the scent intensity of which, at no time, need be substantially greater than such comparable existing products.

It is another object of the present invention to provide a novel sachet product the scent longevity of which is substantially longer than comparable existing products, but which is not dependant on post-purchase scent augmentation through the addition of scented materials.

It is another object of the present invention to provide a novel sachet product the scent longevity of which is substantially longer than comparable existing products, but the manufacture of which is neither complex nor unduly expensive.

It is another object of the present invention to provide a novel method for manufacturing a sachet product the scent longevity of which product is substantially longer than comparable existing products.

It is another object of the present invention to provide a novel method for manufacturing a sachet product the scent longevity of which product is substantially longer than comparable existing products, but the scent intensity of which product is substantially constant over the sachet product's useful life.

It is another object of the present invention to provide a novel method for manufacturing a sachet product the scent longevity of which product is substantially longer than comparable existing products, but the scent intensity of which product, at no time, need be substantially greater than such comparable existing products.

It is another object of the present invention to provide a novel method for manufacturing a sachet product the scent longevity of which product is substantially longer than comparable existing products, but which is not dependant on scent post-purchase scent augmentation through the addition of scented materials.

It is another object of the present invention to provide a novel method for manufacturing a sachet product the scent longevity of which product is substantially longer than comparable existing products, but the manufacture of which product is neither complex nor unduly expensive.

In satisfaction of these and related objectives, Applicant's present invention provides a novel and unobvious envelope sachet and method for making the same. Applicant's envelope sachet is constructed in such a manner as to gradually and steadily release scent from an enclosed portion of perfume oil over an extended period of time. Applicant's invention provides the purchasing public with a substantially improved means by which to obtain the benefits of sachets.

An envelope of Applicant's invention, manufactured according to Applicant's method emits its scent for a substantial period of time, even in an unenclosed environment (e.g. in open space as opposed to in a closed drawer, etc.). Tests of envelope sachet 10 by Applicant have revealed a scent longevity of not less than about a year, with a scent longevity of two or more years appearing likely. This compares very favorably to the two to three week scent longevity of a conventional sachet under like conditions.

The physical dimensions of Applicant's envelope sachet also provide all the benefits of a conventional sachet, but in form which can be accommodated virtually without notice in almost any physical space (even in a conventional greeting card-size envelope).

While Applicant's method for producing her envelope sachet is unique, and represents a significant advance over methods of others with like objectives, Applicant's method is quite simple and inexpensive to utilize. Materials for practicing Applicant's method are readily available, and no specialized training or experience is required. In fact, the assembly of Applicant's envelope sachets may well represent another, much needed opportunity for manufacturing work for which developmentally challenged workers may be suitable.

DETAILED DESCRIPTION OF THE PREFERRED EMBODIMENT

Figure 1:
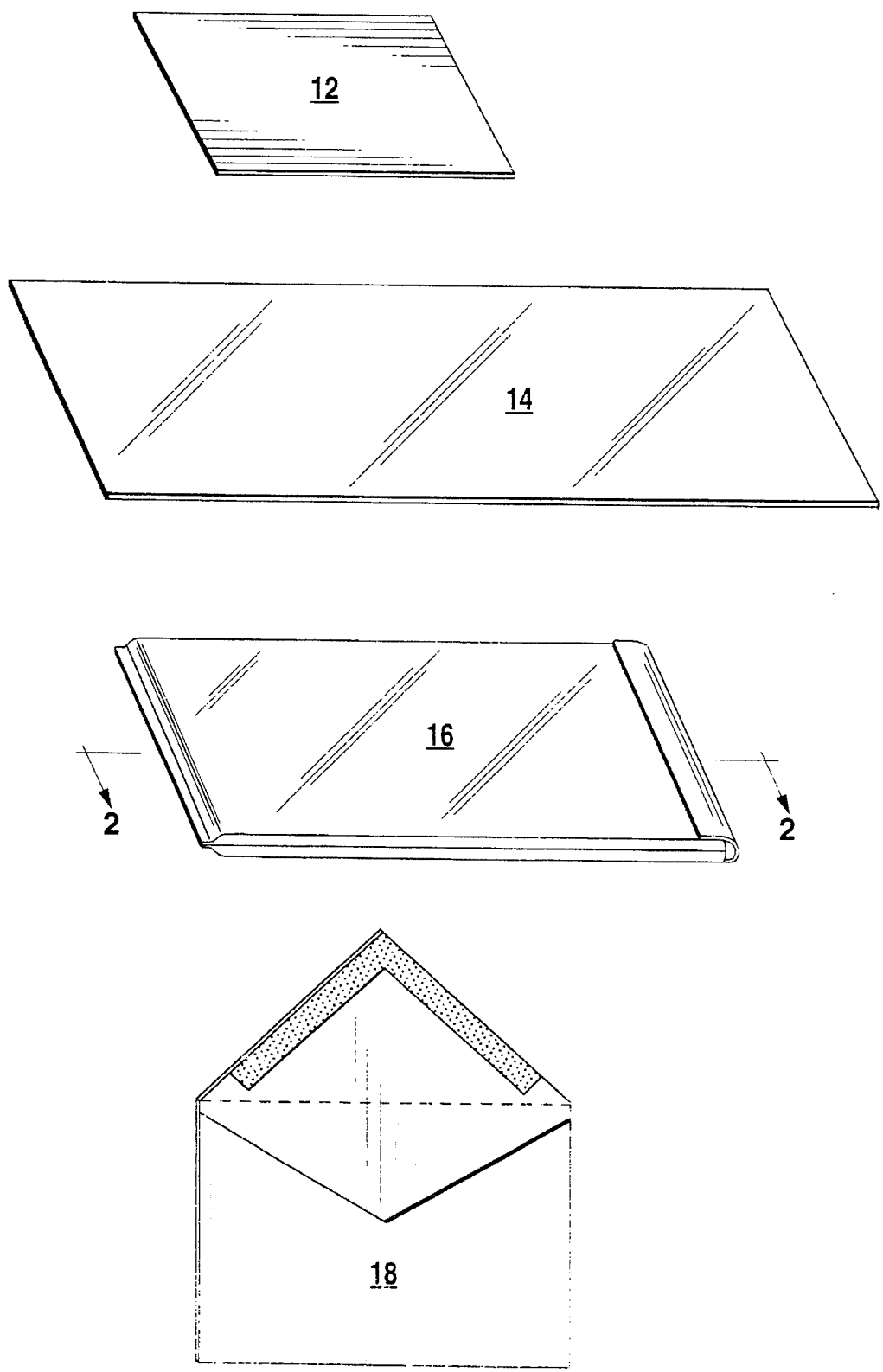
FIG. 1 is an exploded view of the components of Applicant's envelope sachet.
Figure 2:
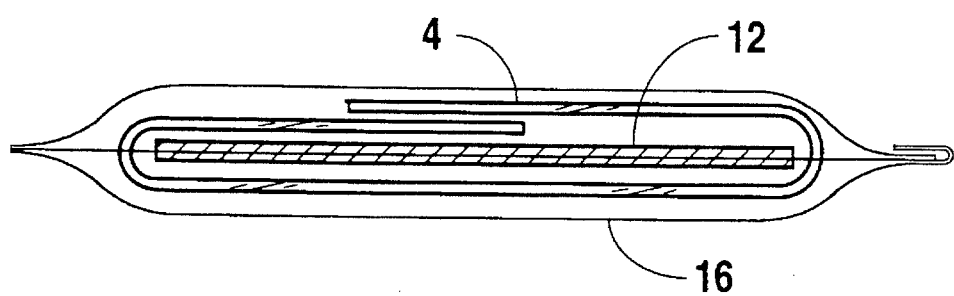
FIG. 2 is a cross-sectional view of a partially assembled envelope sachet of Applicant invention as if shown along Line 2—2.

Referring to FIGS. 1 and 2, the envelope sachet of Applicant's invention is referenced generally by the numeral 10. Envelope sachet 10 is fabricated from four principle, visible elements: a wick sheet 12, a film strip 14, a plastic envelope 16 and a paper envelope 18.

The preferred embodiment of Applicant's envelope sachet includes wick sheet 12 which is a square or rectangular piece of 100 pound blotter paper. In the preferred embodiment of Applicant's envelope sachet 10, the wick sheet 12 is a 2¼"×4" piece of 100 pound blotter paper to which is evenly applied 0.002 pounds (0.032 fl. oz) of perfume oil. In developing the envelope sachet 10, Applicant attempted numerous methods for applying perfume oil to wick sheets 12 such that a substantially correct measure, and even distribution of the oil is achieved.

Rolling, brushing, dipping, wiping, and spraying the oils all provided unsatisfactory results. In some cases, too much or too little oil was applied to any given wick sheet 12. In other cases, oil was concentrated on certain portions of wick sheets 12, but lacking in others. This created oily spots which tended to extrude from the wick sheet and to thereby accelerate the delivery of scent and, in turn, prematurely exhaust the envelope sachet's 10 scent. In still other cases, the expensive perfume oil was consumed in far greater quantities than needed to actually reach the wick sheets 12, thereby drastically increasing the cost of manufacture.

The sole method which has produced satisfactory results, both with respect to quality of application and cost considerations, involved assembling a stack of wick sheets 12 (approximately 30 in number works very well), and tightly binding them as with a multiply-looped rubber band, etc. An applicator bottle (not shown in the drawings, but substantially similar to a common glue bottle) is filled with the appropriate volume of perfume oil for the number of wick sheets 12 to be treated. The oil is then applied with the bottle to all four edge surfaces of the stack (assuming square or rectangular wick sheets 12) carefully insuring that a substantially uniform application of the oil is achieved about all exposed edge surfaces of the wick sheets 12. The wick sheets 12 in the stack are allowed to absorb the oil for approximately an hour before disassembling the stack to continue the assembly of individual envelope sachets.

Wick sheet 12 is wrapped length-wise by film strip 14 which, in the preferred embodiment, is a 2½"×8" strip of 100m-30, 1 MIL. MYLAR—film (the 8" length is a minimum, with no maximum length, except as dictated by practical considerations such as conservation of materials, etc.).

The combined wick sheet 12 and film strip 14 are then enclosed in plastic envelope 16. The plastic envelope 16 of the preferred embodiment of Applicant's envelope sachet is a 2 MIL polyethylene bag (2¾"×5½") with a single opening at a first short end of the bag through which the wick sheet 12 and film strip 14 combination are introduced into the plastic envelope 16.

Once the wick sheet 12 and film strip 14 combination is seated adjacent to the second, closed end of the plastic envelope 16, the portion of the plastic envelope 16 extending beyond the edge of the wick sheet 12 closest to the open end of the plastic envelope 16 is doubled over to overlie an adjacent portion of the plastic envelope 16 and to substantially close the plastic envelope 16 and to thereby enclose the wick sheet 12 and film strip 14 combination within the plastic envelope 16.

Plastic envelope 16 is then enclosed in paper envelope 18 which, in the preferred embodiment, may be of a decorative paper for aesthetic purposes. Paper envelope 18 is preferably a glued flap envelope such as a smaller version of the typical letter or greeting card envelope. The paper envelope 18 is sealed to permanently enclose the plastic envelope, wick sheet 12 and film strip 14 combination and to complete assembly of the envelope sachet 10.

During development and testing of envelope sachet 10 Applicant has determined that envelope sachet 10 exhibits a scent longevity of not less than a year, with indications that a two year scent longevity appears likely.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. An envelope sachet comprising:

a scent wick sheet having first and second broad faces;

an elongate film strip, said film strip being sized and shaped for simultaneously overlying at least a substantial portion of said first broad face and said second broad face of said wick sheet;

a plastic envelope having an plastic envelope opening and occluding means for substantially occluding said envelope opening, said plastic envelope defining an interior envelope space sized and shaped for receiving, within said interior envelope space, said wick sheet with said film strip positioned for simultaneously overlying said first and second broad faces of said wick sheet; and a paper envelope, said paper envelope defining an interior paper envelope space sized and shaped for receiving, within said interior paper envelope space, said plastic envelope with said wick sheet and said film strip enclosed within said plastic envelope.

2. A method for fabricating a sachet comprising the steps of:

selecting a wick sheet and applying a portion of scent composition to said wick sheet;

selecting an elongate film strip which is sized and shaped for encircling and substantially enveloping said wick sheet and encircling said wick sheet with said film strip insuring that edges of said film strip remain substantially unbonded; and selecting a plastic envelope having a plastic envelope opening, placing within an interior plastic envelope space said wick sheet, which said wick sheet is substantially enveloped by said film strip, and substantially closing, but not sealing, said plastic envelope opening and enclosing said wick sheet and said film strip combination within said plastic envelope.

3. The method of claim 2 wherein said wick sheet is fabricated from blotter paper.

4. The method of claim 3 wherein said film strip is fabricated from MYLAR film.

5. The method of claim 4 wherein said plastic envelope is fabricated from polyethylene.

6. The method of claim 2 wherein said film strip is fabricated from MYLAR film.

7. The method of claim 2 wherein said plastic envelope is fabricated from polyethylene.

8. A method for fabricating a sachet comprising the steps of:

selecting a wick sheet and applying a portion of scent composition to said wick sheet;

selecting a film strip which is sized and shaped for encircling and substantially enveloping said wick sheet and encircling said wick sheet with said film strip; and selecting a plastic envelope having a plastic envelope opening, placing within an interior plastic envelope space said wick sheet, which said wick sheet is substantially enveloped by said film strip, and substantially closing said plastic envelope opening and enclosing said wick sheet and said film strip combination within said plastic envelope;

said scent composition is applied by:

assembling a plurality of wick sheets into a stack;

evenly applying a measure of said scent composition to faces of said stack which comprise peripheral edges of said wick sheets; and allowing said scent composition to soak into said into said wick sheets before disassembling said stack.

9. The method of claim 8 wherein said scent composition is a perfume oil.

* * * * *